United States Patent [19]

Kitai et al.

[11] 4,072,060

[45] Feb. 7, 1978

[54] APPARATUS FOR SAMPLING PRINTED SHEETS FROM A CONTINUOUS STREAM OF SUCH SHEETS

[75] Inventors: Mitsuo Kitai, Kawasaki; Koichi Yamashita, Yokohama, both of Japan

[73] Assignee: Kabushiki Kaisha Tokyo Kikai Seisakusho, Tokyo, Japan

[21] Appl. No.: 776,897

[22] Filed: Mar. 11, 1977

[30] Foreign Application Priority Data

Mar. 22, 1976 Japan .................................. 51-29848

[51] Int. Cl.² .............................................. G01N 1/04
[52] U.S. Cl. ................................................ 73/423 R
[58] Field of Search ........................... 73/421 R, 423 R

[56] References Cited

U.S. PATENT DOCUMENTS 2,939,210   6/1960   Cannan ............................... 73/421 R
3,435,685   4/1969   Watkin ................................ 73/421 R Primary Examiner—S. Clement Swisher Attorney, Agent, or Firm—Armstrong, Nikaido & Marmelstein

[57] ABSTRACT

Sampling apparatus for installation on a predetermined path along which sets of printed and folded sheets are fed in overlapping relationship from the folder to the counter-stacker of a web-fed rotary press. The sampling apparatus comprises a divider mechanism which includes a divider blade and which is pivoted by a fluid actuated cylinder to and away from a working position, in which position the divider blade is disposed in the printed sheet path to cause several consecutive ones of the printed sheet sets to travel on one of its sides, where the path is open to a sample exit, and the succeeding printed sheet sets to travel on its other side. Immediately following the movement of the divider mechanism to the working position, an extractor mechanism comprising a pair of extractor blades is pivoted by another cylinder past the printed sheet path for delivering out of the sample exit at least the last of the several consecutive printed sheet sets travelling on the said one side of the divider blade.

7 Claims, 6 Drawing Figures

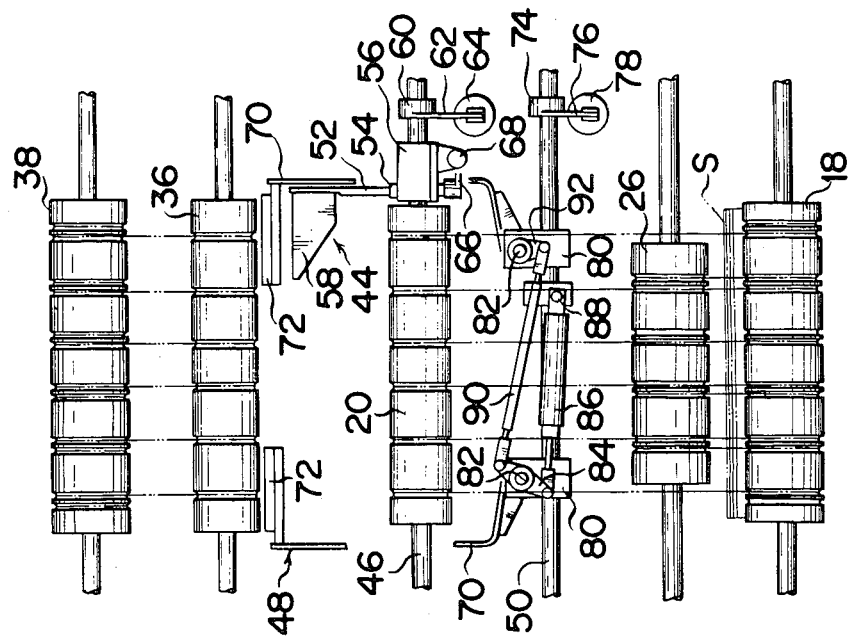
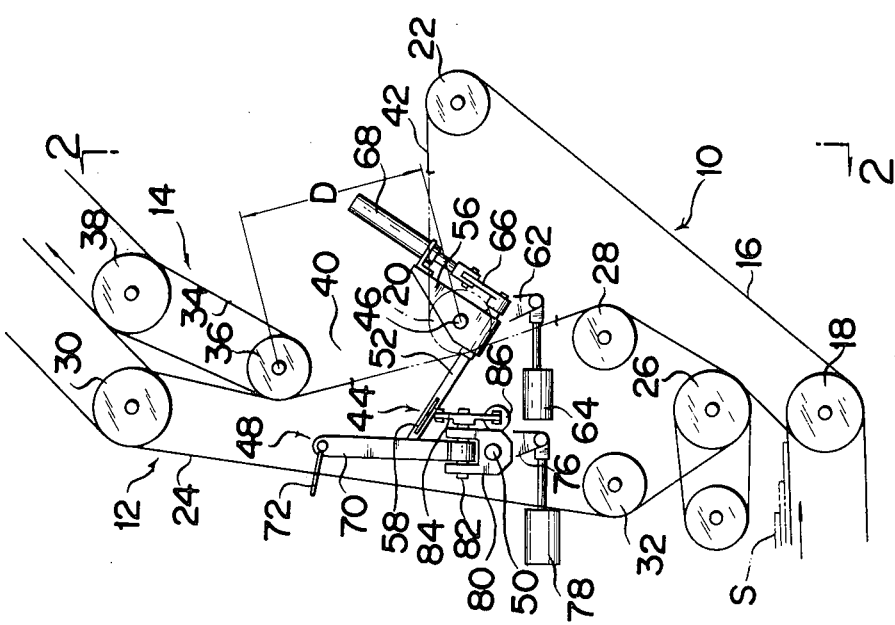

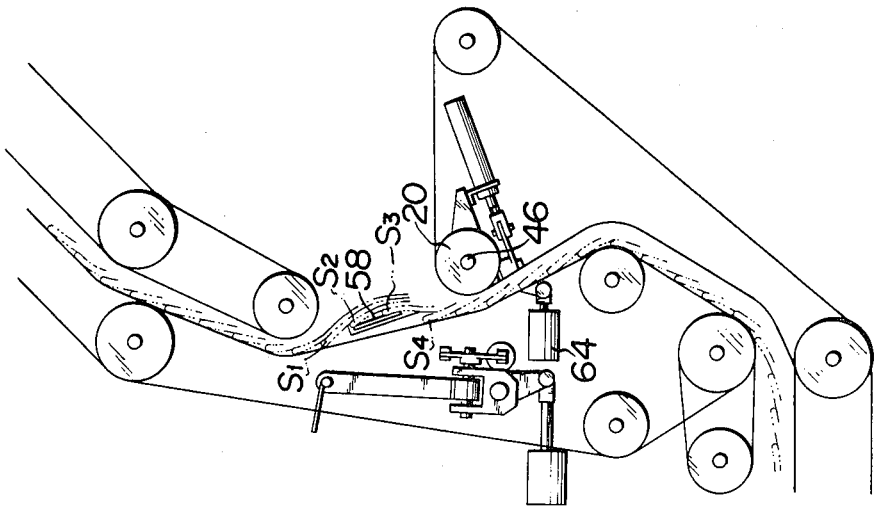
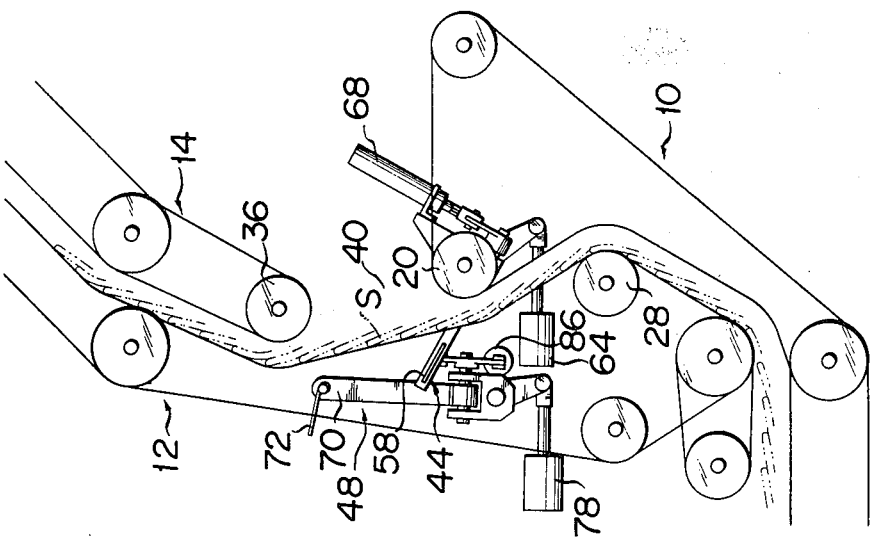

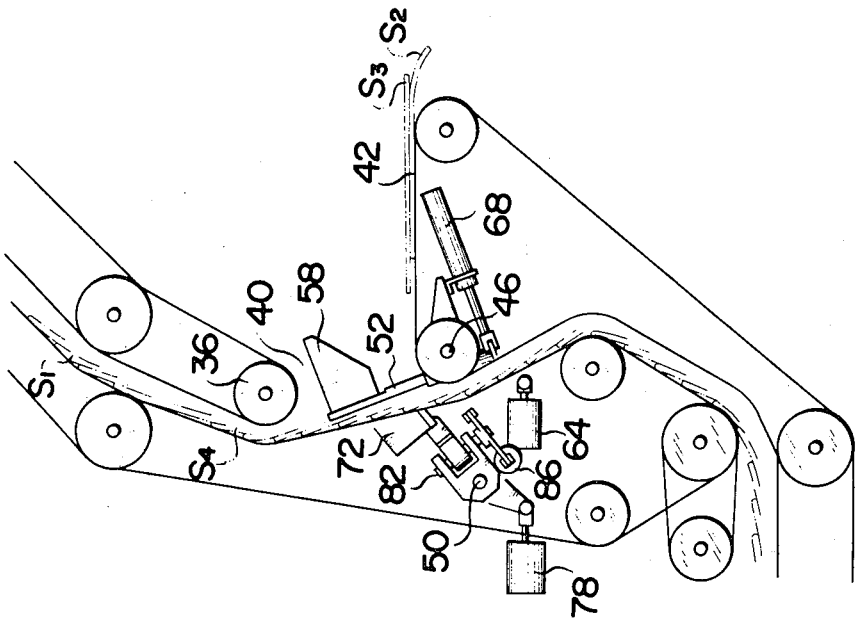
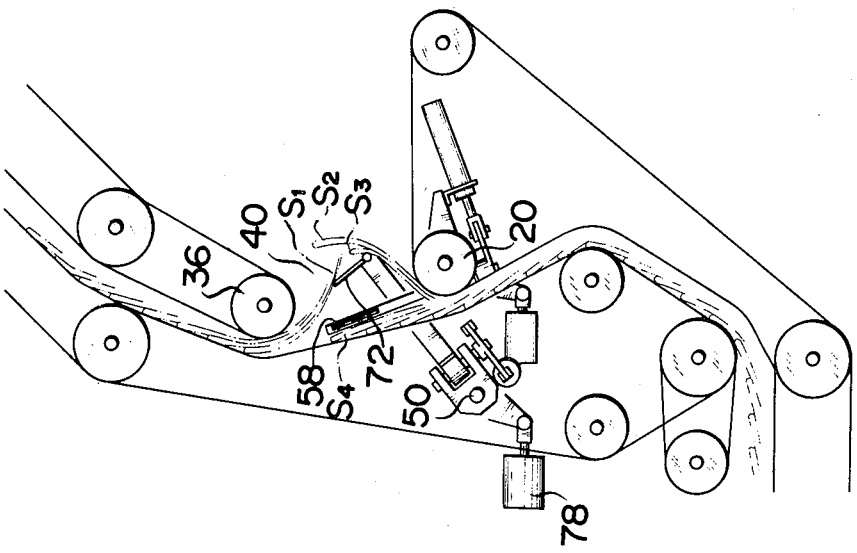

APPARATUS FOR SAMPLING PRINTED SHEETS FROM A CONTINUOUS STREAM OF SUCH SHEETS

BACKGROUND OF THE INVENTION

Our invention relates to sampling apparatus, and more specifically to apparatus for taking samples from a continuous stream of printed sheets to enable the inspector to see if they are printed or folded properly or to check them for other inspection items. Still more specifically, our invention is directed to such sampling apparatus particularly well adaptable for use with a web-fed rotary press, for sampling sets or "signatures" of printed and folded sheets as they are delivered from the folder to the counter-stacker of the press, among other applications.

Heretofore, the sampling of sets of printed and folded sheets travelling at high speed in a continuous, overlapping row from the folder to the counter-stacker of a rotary press has usually been the manual job of skilled inspectors. The manual sampling operation is so difficult, however, that the inspectors have inevitably often disarranged the row of printed sheet sets during extraction of samples therefrom, resulting in the trouble of the counter-stacker or other subsequent equipment.

We are aware of a device already proposed and used for automatically withdrawing damaged or otherwise faulty printed sheets from a continuous stream of such sheets. This prior art device is not suitable for sampling operation, however, since the device withdraws at least seven or so sheets or sets of sheets at one time, compared with about two ordinarily required for inspection purposes.

SUMMARY OF THE INVENTION

It is therefore an object of our invention to provide apparatus for taking a minimum required number of samples from a continuous stream of printed sheets.

Another object of our invention is to provide apparatus capable of taking samples from a continuous stream of printed sheets without disarranging the other sheets.

A further object of our invention is to provide sampling apparatus such that the number of samples to be taken at one time is easily variable as required.

A further object of our invention is to provide sampling apparatus which, after each sampling operation, can be returned to an initial condition without interfering with the travel of printed sheets along a predetermined path and which can thus be held standing by for immediate commencement of the next sampling operation.

A further object of our invention is to provide sampling apparatus which readily lends itself to automation.

A still further object of our invention is to provide sampling apparatus which can be easily installed on a delivery path of printed sheets without major alteration of existing equipment and which requires little installation space.

Summarized in its perhaps broadest aspect, the sampling apparatus in accordance with our invention comprises divider means moved by first actuator means between a first and a second position with respect to a predetermined path along which printed sheets are fed in overlapping relationship, and extractor means moved by second actuator means between a third and a fourth position past the predetermined path. When moved from the first to the second position, the divider means is disposed in the predetermined path so as to cause several consecutive ones of the printed sheets to travel on one side thereof and the succeeding printed sheets to travel on the other side thereof. Following the movement of the divider means to the second position, the extractor means is moved from the third to the fourth position for traversing the predetermined path from said other to said one side of the divider means and thus for extracting at least the last of the said several consecutive printed sheets from the predetermined path.

In a preferred embodiment of our invention, the sampling apparatus is adapted for use wih a web-fed rotary press, for taking samples from a row of overlapping sets of printed and folded sheets being fed by belt conveyors or feeders from the folder to the counter-stacker of the press. The belt conveyors are adapted to provide a sample exit such that when the divider means is moved to the second position, the said one side thereof is open to the sample exit. As the extractor means subsequently traverses the printed sheet path, therefore, a sample set or sets of printed sheets are delivered out of the sample exit, while the divider means coacts with the belt conveyors to prevent the consequent disarrangement of the remaining sets of printed sheets. The number of samples to be taken at one time is variable merely by changing the dimension of the sample exit in the longitudinal direction of the printed sheet path.

The above and other objects, features and advantages of our invention and the manner of attaining them will become more apparent, and the invention itself will best be understood, from the following description of the preferred embodiment taken together with the accompanying drawings.

BRIEF DESCRIPTION OF THE DRAWINGS

FIG. 1 is a schematic elevational view of the sampling apparatus constructed in accordance with our invention, with the apparatus being shown adapted for sampling sets of printed and folded sheets as they are delivered by a web-fed rotary press;

FIG. 2 is a vertical sectional view taken along the line 2—2 of FIG. 1 and showing the sampling apparatus as seen in the direction of the arrows;

FIG. 3 is a view similar to FIG. 1 and explanatory of the way the sets of printed and folded sheets are fed along the predetermined path while the sampling apparatus is held standing by; and FIGS. 4A, 4B and 4C are also views similar to FIG. 1 and explanatory of the sequential steps of the operation of the sampling apparatus.

DESCRIPTION OF THE PREFERRED EMBODIMENT

In one adaptation of our invention shown in the accompanying drawings, the sampling apparatus is installed on a path along with sets of printed sheets S are delivered completely folded from the folder to the counter-stacker, both not shown, of a web-fed rotary press. As will be apparent from FIGS. 1 and 2, the printed sheet path includes an upright portion which is formed by three belt conveyors or feeders 10, 12 and 14.

The first belt conveyor 10 comprises a plurality of endless belts 16 extending in parallel spaced relationship around three grooved rollers 18, 20 and 22. The second belt conveyor 12 comprises a plurality of endless belts 24 extending in parallel spaced relationship around four grooved rollers 26, 28, 30 and 32. The third belt conveyor 14 comprises a plurality of endless belts 34 extending in parallel spaced relationship around two grooved rollers 36 and 38. The successive sets of printed sheets S are to be fed upwardly in overlapping relationship along the upright path by the three belt conveyors 10, 12 and 14, as best shown in FIG. 3.

It will be noted from FIG. 1 that the first and the third belt conveyors 10 and 14 are set apart from each other to provide a sample exit 40 on the front or right hand side of the upright printed sheet path. The first belt conveyor 10 is further adapted to provide a sample path 42 branching from the upright printed sheet path for delivery of sample sets of printed sheets from the sample exit 40 to another location.

Of the two belt conveyor rollers 20 and 36 bounding the sample exit 40, the roller 36 is adjustably movable toward and away from the roller 20 for varying the distance D therebetween, that is, the dimension of the sample exit in the longitudinal direction of the printed sheet path, for purposes hereinafter made apparent. As will be noted from FIG. 2, the second belt conveyor 12 is significantly less in width than the first and the third belt conveyors 10 and 14. The reason for this will also become apparent presently.

The sampling apparatus for combined use with the belt conveyors of the foregoing configuration broadly comprises a divider mechanism 44 mounted on the shaft 46 of the first belt conveyor roller 20, and an extractor mechanism 48 mounted on a shaft 50 extending parallel to the shaft 46. The first belt conveyor roller 20 is an idler and is loosely mounted on the shaft 46.

The divider mechanism 44 comprises an arm or shaft 52 disposed at right angles with the first belt conveyor roller shaft 46 and journalled at or adjacent one end in a bearing 54 integral with a bracket 56 fixedly mounted on the first belt conveyor roller shaft, and a divider blade 58 secured to the other end of the divider arm at a right angle thereto. Also fixedly mounted on the first belt conveyor roller shaft 46 is a collar 60 which is integrally provided with a crank arm 62. This crank arm is knuckle jointed to the piston rod of a fluid actuated cylinder 64 adapted to impart bidirectional rotation to the first belt conveyor roller shaft 46 through a predetermined angle. the cylinder 64 will hereinafter be referred to as the first divider cylinder.

Projecting out of the bearing 54, the said one end of the divider arm 52 is secured to a crank arm 66 which is knuckle jointed to the piston rod of another fluid actuated cylinder 68. This cylinder, hereinafter referred to as the second divider cylinder, is pivotally mounted on the bracket 56 for rotating the divider arm 52 about its own longitudinal axis in either direction through an angle of at least 90 degrees.

As will be apparent from the foregoing, the divider mechanism 44 comprising arm 52 and blade 58 is pivoted by the first divider cylinder 64 about the axis of the first belt conveyor roller shaft 46 between a first or retracted position shown in FIGS. 1 and 3 and a second or working position shown in FIGS. 4A and 4B. The divider blade 58 is further pivoted by the second divider cylinder 68 about the longitudinal axis of the divider arm 52 between a working position shown in FIGS. 1, 2, 3, 4A and 4B, where the divider blade is disposed substantially crosswise with the row of the sets of printed sheets S, and a retracted position shown in FIG. 4C, where the divider blade is angularly spaced at least 90 degrees from its working position.

It will be observed from FIG. 4A that when pivoted to its second position, the divider mechanism 44 has its divider blade 58, which is then in its working position as shown, disposed in the printed sheet path so as to cause some consecutive ones of the printed sheet sets to travel on its front side, where the printed sheet path is open to the sample exit 40, and the succeeding printed sheet sets to travel on its rear side. As will be seen from FIG. 2, the arm 52 of the divider mechanism 44 is pivotable between the first and the second positions without interfering with the progress of the printed sheet sets along the predetermined path.

The extractor mechanism 48 comprises a pair of arms 70 each supported at one end on the shaft 50 in the manner hereinafter described, and a pair of extractor blades 72 secured to the other ends of the extractor arms in right angular relationship, respectively. The shaft 50 has a collar 74 fixedly mounted thereon, which collar is integrally provided with a crank arm 76. This crank arm is knuckle jointed to the piston rod of a fluid actuated cylinder 78, hereinafter referred to as the first extractor cylinder, that is adapted to impart bidirectional rotation to the shaft 50 through a predetermined angle.

Also fixedly mounted on the shaft 50 are a pair of spaced-apart lugs 80 each rotatably supporting a pivot pin 82 disposed at right angles with the shaft 50. The pair of extractor arms 70 are secured to the respective pivot pins 82 for pivotal movement toward and away from each other. The left hand one, as viewed in FIG. 2, of the pivot pins 82 is further rigidly connected to a crank arm 84 at its midpoint. This crank arm is knuckle jointed at one end to the piston rod of a fluid actuated cylinder 86, hereinafter referred to as the second extractor cylinder, that is pivoted at 88 on the shaft 50. At the other end the crank arm 84 is knuckle jointed to a link 90 and thence to another crank arm 92 rigidly connected to the right hand pivot pin 82.

The extractor mechanism 48 comprising the pair of extractor blades 72 supported by the respective arms 70 is therefore pivoted about the shaft 50 by the first extractor cylinder 78 between a third position shown in FIGS. 1, 3 and 4A and a fourth position shown in FIGS. 4B and 4C. The pair of extractor arms 70 together with the extractor blades 72 thereon are further pivoted about the respective pivot pins 82 by the second extractor cylinder 86 between working positions best shown in FIG. 2 and retracted positions shown in FIG. 4C.

As will be noted from FIG. 12, the pair of extractor blades 72 when in their working positions extend substantially across the row of printed sheets sets S travelling along the predetermined path, with a spacing therebetween which is considerably less than the width of the printed sheet sets and which is slightly more than the width of the second belt conveyor 12. When in their retracted positions as shown in FIG. 4C, the pair of extractor blades 72 have a spacing therebetween greater than the width of the printed sheet sets. The pair of extractor arms 70 are of course pivotable between the aforesaid third and the fourth positions of the extractor mechanism without interfering with the travel of the printed sheet sets along the predetermined path regardless of whether the extractor arms are pivoted toward or away from each other.

The extractor mechanism 48 is to be pivoted from the third to the fourth position, with the pair of extractor blades 72 held in their working positions, immediately following the pivotal movement of the divider mechanism 44 from the first to the second position. As will be seen from FIG. 4B, the pair of blades 72 of the extractor mechanism on its way from the third to the fourth position traverses the printed sheet path from the rear to the front side of the divider blade 58 and, in so doing, extracts toward the sample exit 40 at least the last of the several sets of printed sheets travelling on the front side of the divider blade. The extracted sample set of printed sheets is delivered onto the sample path 42 via the sample exit.

OPERATION

While the operation of the sampling apparatus in accordance with our invention is believed to have been largely understood from the foregoing description, further amplification will be made in the following brief summary of such operation. FIG. 3 illustrates the sampling apparatus in a standby condition, while the sets of printed and folded sheets S are shown being fed at relatively high speed along the upright path in overlapping relationship by the three belt conveyors 10, 12 and 14.

Although the upright printed sheet path is open at the sample exit 40, there is no possibility of the printed sheet sets deviating into the sample exit while the sampling apparatus is held standing by, mainly because they are pressed so firmly against the first belt conveyor 10 by the roller 28 of the second belt conveyor 12 immediately before passing the sample exit. It is also important to mention that the distance D between the conveyor rollers 20 and 36 bounding the sample exit is less than the length of each set of printed sheets, that is, the dimension of each printed sheet set in the longitudinal direction of the printed sheet path, even when the distance D is maximized by moving the conveyor roller 36 away from the conveyor roller 20.

For holding the sampling apparatus standing by as shown in FIG. 3, the first divider cylinder 64 may be extended to hold the divider mechanism 44 in the first position. The second divider cylinder 68 may be retracted to hold the divider blade 58 in the working position. The first extractor cylinder 78 may be extended to hold the extractor mechanism 48 in the third position. The second extractor cylinder 86 may be extended to hold the pair of extractor arms 70 pivoted toward each other and thus to hold the pair of extractor blades 72 in their working positions.

Reference is now directed to FIGS. 4A, 4B and 4C to describe the operation of the sampling apparatus as adapted specifically for taking two samples at one time from the continuous stream of the printed sheet sets S. The operation of the sampling apparatus commences as the operator causes the first divider cylinder 64 to retract its piston rod, with the result that the divider mechanism 44 is pivoted about the first belt conveyor roller shaft 46 from the first to the second position.

As clearly shown in FIG. 4A, the divider mechanism 44 when pivoted to the second position has its divider blade 58 disposed in the upright printed sheet path, causing several consecutive ones of the overlapping printed sheet sets to travel on its front side and the succeeding sets to travel on its rear side. Attention should be paid to the four consecutive sets of printed sheets designated S1, S2, S3 and S4, respectively. S1, S2 and S3 represent the last three of the several consecutive printed sheet sets travelling on the front side of the divider blade 58, and S4 represents the first of the succeeding printed sheet sets travelling on its rear side.

With reference to FIG. 4B, the first extractor cylinder 78 may be retracted to pivot the extractor mechanism 48 about the shaft 50 from the third to the fourth position immediately following the movement of the divider mechanism from the first to the second position. On its way from the third to the fourth position, the extractor mechanism 48 should traverse the printed sheet path just when the printed sheet set S1 becomes caught between the second belt conveyor 12 and the third belt conveyor roller 36. In this manner the pair of extractor blades 72 operates to raise the trailing end of the printed sheet set S1 away from the second belt conveyor 12 and, at the same time, to push out of the sample exit 40 the last two S2 and S3 of the several consecutive printed sheet sets that have been travelling on the front side of the divider blade 58.

By the time when the two sample sets of printed sheets S2 and S3 are extracted out of the sample exit 40 in the above described manner, the first S4 of the succeeding printed sheet sets is caught sufficiently between the divider blade 58 and the second belt conveyor 12, so that the succeeding printed sheet sets will not follow the samples into the sample exit 40. The pair of extractor blades 72 may hit the succeeding printed sheet set S4 if there is an irregularity in the pitch of the successive printed sheet sets, or if they are disarranged. Even in this case the divider blade 58 will serve to prevent the consequent displacement or deviation of the succeeding printed sheet set S4 into the sample exit 40.

On emerging from the divider blade 58, the succeeding printed sheet set S4 will lap under the printed sheet set S1 which has been just released by the pair of extractor blades 72, and these together with the other remaining printed sheet sets will continue travelling toward the counter-stacker along the predetermined path as shown in FIG. 4C. Simultaneously, the two extracted sample sets S2 and S3 will travel away from the sample exit 40 along the sample path 42.

The divider mechanism 44 and the extractor mechanism 48 must then be returned to the initial positions of FIG. 3 without interfering with the travel of the printed sheet sets S along the predetermined path. It is to this end that the second divider cylinder 68 and the second extractor cylinder 86 are provided.

For returning the divider mechanism 44 from the second to the first position, the second divider cylinder 68 may first be extended to pivot the divider blade 58 about the longitudinal axis of the divider arm 52 from the working to the retracted position shown in FIG. 4C, with the retracted position being angularly spaced at least 90° from the working position. The first divider cylinder 64 may then be extended to pivot the divider mechanism 44 about the first belt conveyor roller shaft 46 from the second to the first position. In this manner the divider mechanism can be returned to the first position without interfering with the travel of the printed sheet sets along the predetermined path, since the divider blade 58 when in its retracted position passes outside the printed sheet path.

For returning the extractor mechanism 48 from the fourth to the third position, the second extractor cylinder 86 may first be retracted to pivot the pair of extractor arms 70 away from each other about the respective pivot pins 82, thereby providing between the pair of extractor blades 72 a spacing greater than the width of the printed sheet sets. By then extending the first extractor cylinder 78, the extractor mechanism 48 can be pivoted about the shaft 50 from the fourth to the second position without interfering with the travel of the printed sheet sets along the predetermined path.

Following the return of the divider mechanism 44 and the extractor mechanism 48 to the first and third positions, respectively, the second divider cylinder 68 may be retracted to pivot the divider blade 58 from the retracted to the working position. The second extractor cylinder 86 may be extended to pivot the pair of extractor arms 70 toward each other and hence to move the pair of extractor blades 72 back to their working positions. One cycle of sampling operation is now completed, and the sampling apparatus may be held standing by for the next sampling operation.

The sampling apparatus for use with a web-fed rotary press or the like is usually required to take two samples at one time as in the foregoing adaptation of our invention. The sampling apparatus in accordance with our invention, however, is readily adaptable for taking one or three samples at one time.

For taking one sample at one time by the illustrated sampling apparatus, the third belt conveyor roller 36 may be moved closer to the first belt conveyor roller 20. Thus, when the extractor mechanism 48 traverses the row of printed sheet sets S following the movement of the divider mechanism 44 from the first to the second position, as shown in FIG. 4B, the printed sheet sets S1 and S2 will already be caught between the second belt conveyor 12 and the third belt conveyor roller 36, so that only the printed sheet set S3 will be extracted out of the sample exit 40.

The third belt conveyor roller 36 may be moved farther away from the first belt conveyor roller 20 for taking three samples at one time. With the distance D between the rollers 20 and 36 thus increased, the printed sheet set S1 will not yet be caught between the second belt conveyor 12 and the third belt conveyor roller 36 when the extractor mechanism 48 traverses the row of printed sheet sets following the movement of the divider mechanism 44 from the first to the second position. As a consequence, the three printed sheet sets S1, S2 and S3 will all be extracted out of the sample exit 40.

It will now be apparent that the sampling apparatus in accordance with our invention extracts as a sample at least the last of the several printed sheet sets travelling on the front side of the divider blade 58 in its working position, practically without any possibility of disarranging the other printed sheet sets in so doing. It will also have been understood that the sampling apparatus of the foregoing construction is well calculated to permit easy installation on the existing path for the delivery of printed sheet sets from the folder to the counter-stacker of the rotary press.

The sampling apparatus in accordance with our invention is also well calculated to lend itself to easy automation so that, once its operation is commenced by the operator, the above described complete cycle of sampling operation may be performed fully automatically. Such automatic operation of the sampling apparatus can be controlled electrically, in relation to the production speed of the rotary press. The use of electrical control signals is particularly desirable for operating the first divider cylinder 64 and the first extractor cylinder 78 one after the other, in order that the extractor mechanism 48 may move from the third to the fourth position immediately following the movement of the divider mechanism 44 from the first to the second position, in timed relationship to the travelling speed of the printed sheet sets along the predetermined path.

Having thus described our invention, we believe that the objects as above stated have been attained in a simple and thoroughly practicable manner. We also understand, however, that our invention is not to be restricted by the exact details of this disclosure, since numerous modifications or changes of the invention will readily occur to those skilled in the art without departing from the spirit or scope of the following claims.

We claim:

1. Apparatus for taking samples from a continuous row of printed sheets travelling in overlapping relationship along a predetermined path, comprising in combination:

divider means movable between a first and a second position with respect to the predetermined path, said divider means when moved to said second position being disposed in the predetermined path so as to cause some consecutive ones of the printed sheets to travel on one side thereof and the succeeding printed sheets to travel on the other side thereof;

first actuator means for moving said divider means between said first and said second positions;

extractor means movable between a third and a fourth position past the predetermined path, said extractor means being moved, following the movement of said divider means from said first to said second position, from said third to said fourth position for traversing the predetermined path from said other to said one side of said divider means and thus for extracting at least the last of said some consecutive printed sheets from the predetermined path; and second actuator means for moving said extractor means between said third and said fourth positions.

2. The sampling apparatus as recited in claim 1, further comprising means for permitting said divider means to return from said second to said first position without interfering with the travel of the printed sheets along the predetermined path, and means for permitting said extractor means to return from said fourth to said third position without interfering with the travel of the printed sheets along the predetermined path.

3. The sampling apparatus as recited in claim 2, wherein said divider means comprises:

an arm supported at one end so as to be both pivotable about an axis extending across the row of printed sheets and rotatable about its own longitudinal axis at right angles with the first mentioned axis, said arm being pivoted about the first axis between said first and said second positions of said divider means by said first actuator means without interfering with the travel of the printed sheets along the predetermined path; and a divider blade fixedly mounted on the other end of said arm;

and wherein said means for permitting said divider means to return comprises:

third actuator means for rotating said arm about its own longitudinal axis;

whereby said divider blade is angularly displaced about the longitudinal axis of said arm between a working position, where said divider blade extends substantially crosswise with the row of printed sheets, and a retracted position angularly spaced at least 90° from said working position, said divider blade being held in said retracted position during the return of said divider means from said second to said first position.

4. The sampling apparatus as recited in claim 2, wherein said extractor means comprises:

a pair of arms supported each at one end so as to be both pivotable around a first axis extending across the row of printed sheets and pivotable toward and away from each other about respective second axes at right angles with said first axis, said pair of arms being jointly pivoted about said first axis between said third and said fourth positions of said extractor means by said second actuator means without interfering with the travel of the printed sheets along the predetermined path regardless of whether said arms are held pivoted toward or away from each other; and a pair of extractor blades each fixedly mounted on the other end of one of said pair of arms so as to extent toward each other substantially across the row of printed sheets when said arms are held pivoted toward each other;

and wherein said means for permitting said extractor means to return comprises:

third actuator means for pivoting said pair of arms toward and away from each other about said respective second axis;

whereby during the return of said extractor means from said fourth to said third position, said pair of arms are held pivoted away from each other by said third actuator means to provide between said pair of extractor blades a spacing greater than the width of the row of printed sheets.

5. Apparatus for taking samples from a continuous row of printed sheets travelling in overlapping relationship along a predetermined path, comprising in combination:

conveyor means for feeding the row of overlapping printed sheets along the predetermined path, said conveyor means being adapted to provide a sample exit to which is open the predetermined path;

divider means movable between a first and a second position with respect to the predetermined path, said divider means when moved to said second position being disposed in the predetermined path so as to cause some consecutive ones of the printed sheets to travel on one side thereof, where the predetermined path is open to the sample exit, and the succeeding printed sheets to travel on the other side thereof;

first actuator means for moving said divider means between said first and said second positions;

extractor means movable between a third and a fourth position past the predetermined path, said extractor means being moved, immediately following the movement of said divider means from said first to said second position, from said third to said fourth position for traversing the predetermined path from said other to said one side of said divider means and thus for extracting at least the last of said some consecutive printed sheets from the predetermined path, with the extracted printed sheet being delivered out of the sample exit; and second actuator means for moving said extractor means between said third and said fourth positions.

6. The sampling apparatus as recited in claim 5, wherein the dimension of the sample exit in the longitudinal direction of the predetermined path is adjustably variable for changing the number of printed sheets to be extracted by each sampling operation.

7. The sampling apparatus as recited in claim 5, wherein said conveyor means is adapted to provide a sample path branching from the predetermined path through the sample exit.

* * * * *